United States Patent [19]
Goldberg

[11] Patent Number: 4,950,664
[45] Date of Patent: Aug. 21, 1990

[54] NASAL ADMINISTRATION OF BENZODIAZEPINE HYPNOTICS

[75] Inventor: Arthur H. Goldberg, Montclair, N.J.

[73] Assignee: Rugby-Darby Group Companies, Inc., Rockville Centre, N.Y.

[21] Appl. No.: 245,031

[22] Filed: Sep. 16, 1988

[51] Int. Cl.$^5$ .................. A61K 9/08; A61K 47/22; C07D 243/10; C07D 243/20
[52] U.S. Cl. .................. 514/219; 514/159; 514/161; 514/218
[58] Field of Search ............... 424/177, 260; 514/159, 514/161, 218, 219

[56] References Cited

U.S. PATENT DOCUMENTS

| | | | |
|---|---|---|---|
| 4,244,945 | 1/1981 | Wilkinson | 424/177 |
| 4,284,648 | 8/1981 | Hussain et al. | 424/330 |
| 4,786,647 | 11/1988 | Simpkins et al. | 514/355 |
| 4,789,667 | 12/1988 | Makino et al. | 514/161 |

Primary Examiner—John Kight, III
Assistant Examiner—Carlos Azpura
Attorney, Agent, or Firm—Philip M. French

[57] ABSTRACT

Nasal administration of benzodiazepines is described as providing improved therapeutic effects as compared to conventional delivery techniques. The compositions comprise a benzodiazepine hypnotic in a pharmaceutically acceptable nasal carrier.

16 Claims, 3 Drawing Sheets

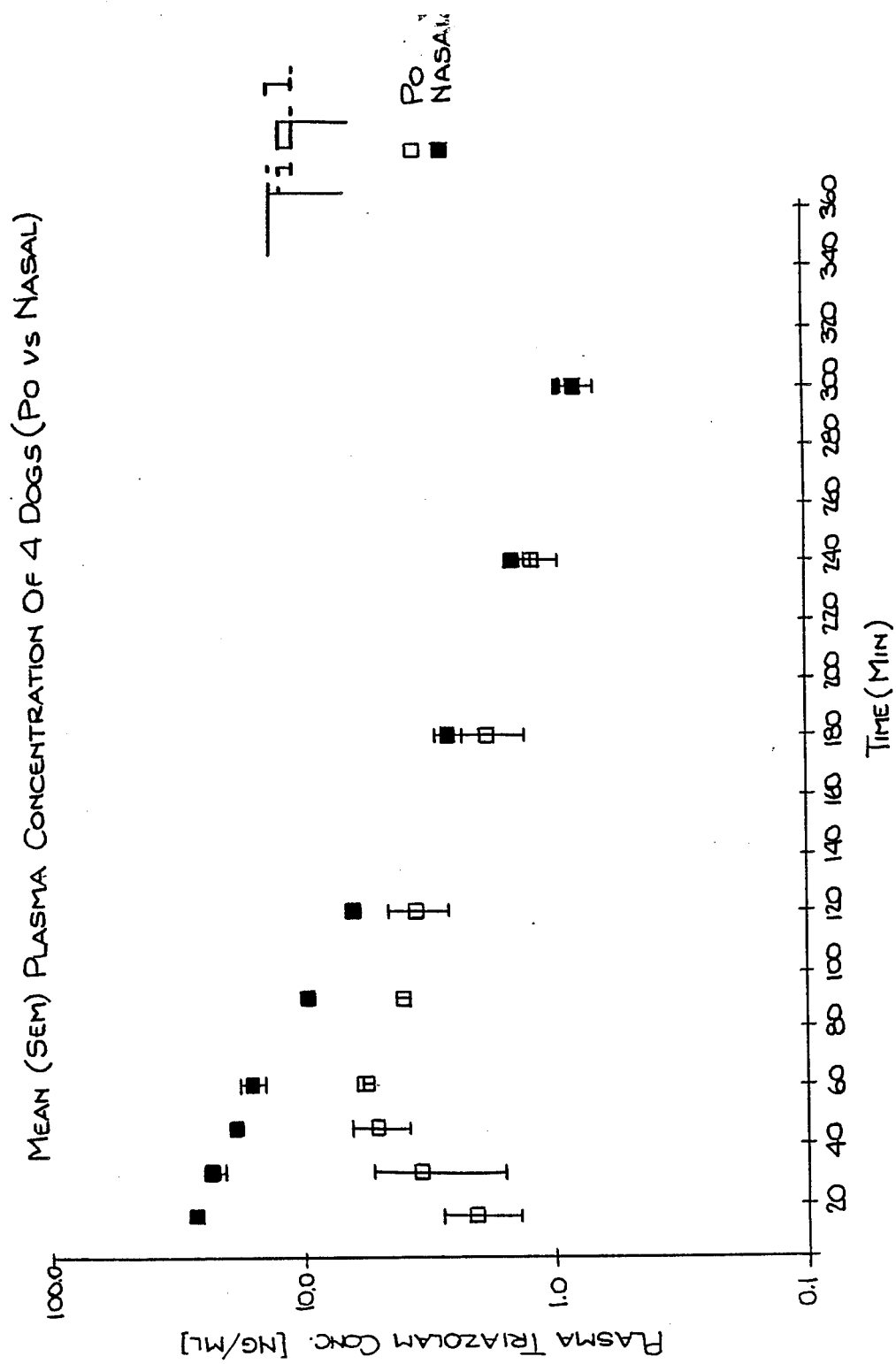

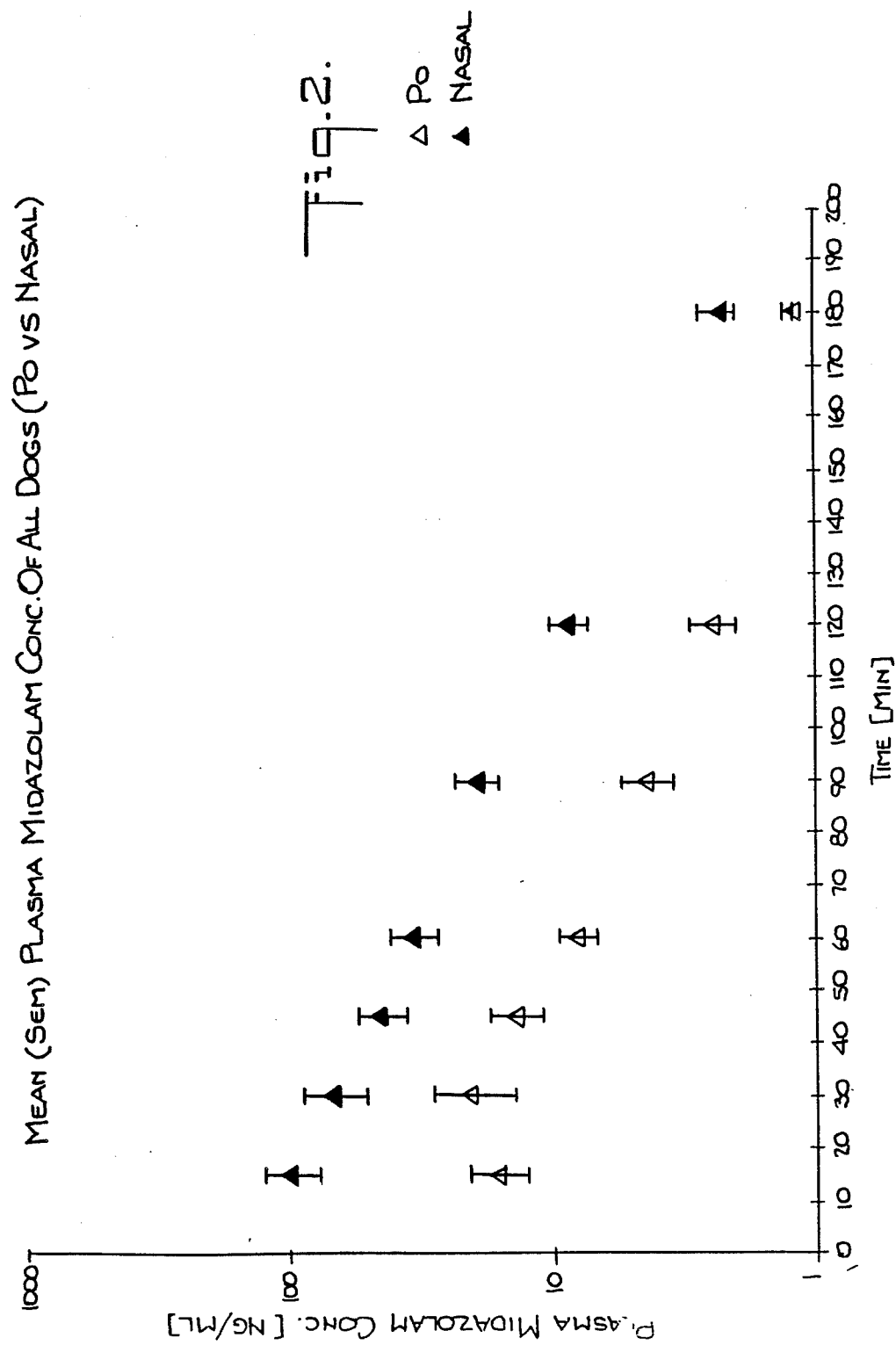

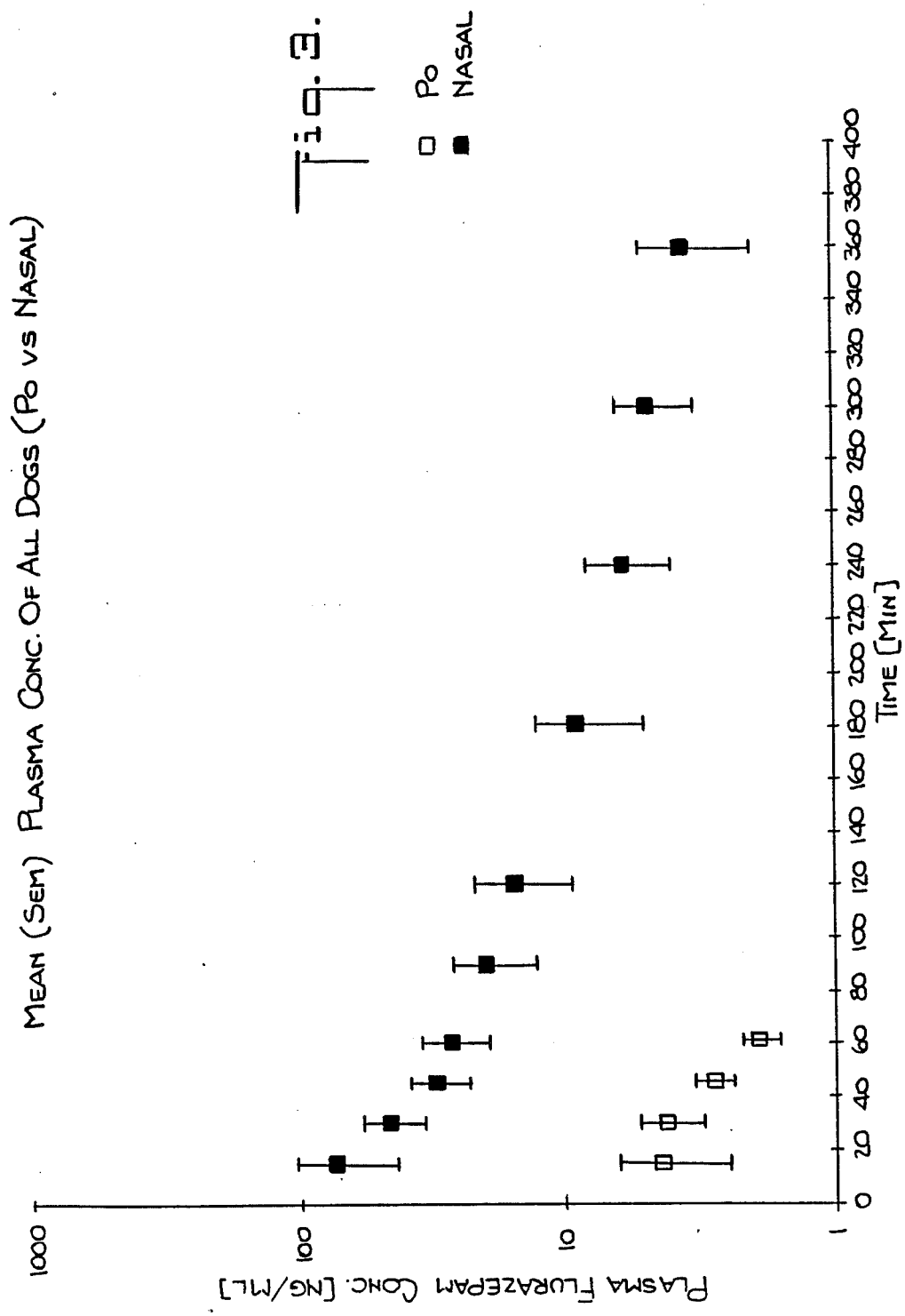

NASAL ADMINISTRATION OF BENZODIAZEPINE HYPNOTICS

BACKGROUND OF THE INVENTION

FIELD OF THE INVENTION

The present invention relates to a novel form of certain hypnotic drugs and to their administration to mammals. They may be employed for any of the conventional purposes for which hypnotics are known, but especially for improving sleep.

Hypnotic drugs are a class of therapeutic agents which are commonly employed to induce and/or to prolong sleep. They may also be utilized to alleviate sleep disorders. Terms such as sedative, anti-anxiety agent, minor tranquilizer and anxiolytic are sometimes used somewhat interchangeably for such drugs because, in appropriate dosages, these hypnotics can produce similar effects.

There are a wide variety of hypnotic drugs. This term includes both barbiturates and non-barbiturates. Typical barbiturate hypnotics are aprobarbital and pentobarbital. Non-barbiturates recognized for their hypnotic activity include benzodiazepines; antihistamines having pronounced side effects such as diphenhydramine; serotonin initiators such as L-tryptophane; and various other drugs including ethinamate, chloral hydrate, ethchlorvynol, methyprylon and glutethimide. Their hypnotic effect is commonly attributed to a neurological mechanism involving depression of the central nervous system. That effect is also frequently accompanied by a mild reduction in such physiological functions as blood pressure and respiration.

PRIOR ART

Numerous hypnotic drugs are already known. Many, for example, are listed in the Physicians Desk Reference (PDR) published by Medical Economics Company, Inc. They are widely used therapeutically to improve sleep. Administration is generally performed either parenterally or, more usually, orally by means of pills, tablets and capsules. Their various uses are likewise well known.

Unfortunately, these drugs commonly exhibit a number of drawbacks when conventionally administered. Some have undesirable side effects. Many are inefficiently and variably absorbed from their current dosage forms. Further, the onset of their pharmacological activity is often delayed and/or the duration of that activity limited pursuant to ordinary oral, subcutaneous and/or intra-muscular administration.

Unlike the broad applicability of conventional routes of administration, the nasal delivery of therapeutic agents is a relatively recently discovered technique. It is also recognized only for specific agents. Representative disclosures of nasal administration of drugs include: U.S. Pat. No. 4,454,140 of Goldberg et al; U.S. Pat. No's. 4,428,883; 4,284,648; and 4,394,390 of Hussain and U.S. Pat. No. 4,624,965 of Wenig.

While nasal administration has become an accepted route of administration, the foregoing disclosures limit that mode of delivery to the specific drugs described. Moreover, it has been observed that many therapeutic agents cannot be usefully administered by this unusual route. Consequently, nasal administration remains a technique for which applicability is far from universal and the results unpredictable.

SUMMARY OF INVENTION

It has been discovered that certain known hypnotic drugs can normally be effectively administered to mammals, and especially to humans, in novel compositions. More specifically, these compositions are ones which contain a benzodiazepine hypnotic adapted for nasal administration and comprise a solution, suspension, ointment, gel or other useful nasal form. These nasal compositions may be employed for any of the known therapeutic purposes for which such hypnotics are known.

The utilization of a nasal form of these hypnotic drugs greatly facilitates administration. As compared with parenteral administration, for example, a simple aerosol container or a dropper will suffice for delivery. From a therapeutic standpoint, nasal administration often provides a hypnotic effect of improved duration. It may also be more efficiently and precisely controlled than through conventional means and permits a more rapid onset of activity. These and additional advantages of the present invention will become evident from the description and examples which follow.

BRIEF DESCRIPTION OF THE DRAWINGS

The invention and particularly the Examples and Tables, will be more clearly understood when considered with the accompanying drawings in which:

FIG. 1 is a graphic depiction of the comparative results of Example 1;

FIG. 2 is a graphic depiction of the comparative results of Example 2; and

FIG. 3 is a graphic depiction of the comparative results of Example 3.

DETAILED DESCRIPTION OF THE INVENTION

Any benzodiazepine drug capable of exhibiting a hypnotic activity may be employed in accordance with the present invention. These particularly include diazepam, triazolam, midazolam, temazepam and flurazepam; although other, less common benzodiazepines may also be utilized.

Any pharmaceutically acceptable form of these benzodiazepine drugs may be utilized in accordance with the present invention. Generally the selected therapeutic agent is provided in the chemical form which has previously been found most efficacious for oral or parenteral delivery. Most commonly, this comprises either the free base or a pharmaceutically acceptable salt of the hypnotic agent.

A peculiar facet of the present invention lies in the discovery of the uniqueness of this class of hypnotics. Despite the recognized equivalence of benzodiazepines with other subclasses of hypnotics, they do not provide the many advantages enjoyed through the nasal administration of benzodiazepines. In fact, it has been discovered that many of these non-benzodiazepine hypnotics fail to exhibit that therapeutic activity when they are administered nasally, instead of by conventional method.

In the formulation of the present hypnotic compositions, a relatively water soluble form of the benzodiazepine is usually employed. Use of a fully dissolved form of the benzodiazepine maximizes its immediate effect. Compositions containing the therapeutic drug in a form having a limited solubility may be employed where sustained release is desired. These compositions, in which the therapeutic drug is not totally solubilized in its dosage form provide a prolonged therapeutic activity. For this purpose, a long chain carboxylic acid salt of the desired drug is often preferred. The acid portion of the salt preferably contains from about 10 to about 30 carbon atoms. Such salts, including stearates, palmitates and the like, are readily synthesized by known techniques.

The dosage forms of the present invention additionally comprise a pharmaceutically acceptable nasal carrier. Any of the benzodiazepines can be conveniently administered in such a carrier. These compositions comprise a systemic, therapeutically effective amount of the desired drug together with a pharmaceutically acceptable nasal carrier therefore.

Nasal carriers suitable in accordance with the present invention will be apparent to those skilled in the art of nasal pharmaceutical formulations. Exemplary nasal carriers include saline solutions; alcohols such as ethanol; glycols such as propylene glycol; glycol ethers such as polyethylene glycol and combinations of the foregoing with water and/or one another. For still other examples, reference is made to the text entitled "REMINGTON'S PHARMACEUTICAL SCIENCES", 14th edition, 1970.

The choice of a suitable carrier in accordance with the present invention will depend on the exact nature of the particular nasal dosage form required. A therapeutic agent may, for example, be formulated into a nasal solution (for use as drops or as a spray), a nasal suspension, a nasal ointment, a nasal gel or any other nasal form. Preferred nasal dosage forms are solutions, suspensions and gels. These normally contain a major amount of water (preferably purified water) in addition to the active hypnotic ingredient. Minor amounts of other ingredients such as tonicity agents (e.g. NaCl) pH adjusters (e.g., a base such as NaOH), emulsifiers or dispersing agents, buffering agents, preservatives, wetting agents and jelling agents (e.g., methylcellulose) may also be present. Particularly preferred compositions contain various of the foregoing other ingredients so as to be isotonic and/or buffered to the same pH as blood serum.

The present compositions may be administered to any of the subjects recognized as being susceptible to benzodiazepine hypnotics. While therefore generally useful in treatment of a broad spectrum of mammals, the present invention is most desirably employed on human subjects.

The efficacy of a hypnotic drug is most clearly revealed by its concentration in the blood of the subject being treated. In general, hypnotic activity is dependent upon the bioavailability of therapeutic agent evidenced by that concentration. It is therefore particularly significant that the present nasal administration of benzodiazepines is characterized by a significantly faster onset and more pronounced blood concentration of hypnotic than conventional forms of administration. This insures an elevated and more constant hypnotic effect.

Those skilled in the art will be aware that a systemic, therapeutically effective amount of a particular benzodiazepine hypnotic will vary with the particular drug as well as the type, age, size, weight and general physical condition of the subject. The amount will also vary dependent upon the particular therapeutic effect desired. Typically the dosage level will be more similar to the expected dosage level for intravenous administration than to the dosage levels currently employed for other methods of administration, for example, oral or rectal.

As a practical matter, the present therapeutic compositions will normally be prepared in dosage unit forms to contain a systemic, therapeutically effective amount of the selected hypnotic drug. This can be similar to conventional dosage amounts of the drug. The drug unit is normally less than 0.2 ml, optimally from 0.05 to 0.1 ml in volume. Desirably, nasal dosage units are prepared having a lesser amount of drug, preferably from one-half to one-tenth of the amount of therapeutic agent employed for conventional routes of administration. This is made possible through the improved blood concentration levels for benzodiazepines which have been observed to result from nasal administration. These are the most preferred types of compositions.

The present compositions are especially useful for improving sleep. They may be utilized to more rapidly induce and/or to prolong sleep. This use is not, however, exclusive. The present invention may likewise be employed to enhance other known therapeutic utilities of benzodiazepines.

The following examples are given by way of illustration only and are not to be considered limitations of this invention. Many apparent variations are possible without departing from the spirit or scope thereof.

EXAMPLE 1

In two comparative studies separated in time by over one week; four healthy male, 2–3 year old beagle dogs received oral and nasal doses of triazolam. They were fasted overnight before each study and food was withheld until the end of the experiment. They were restrained in a dog sling during the studies while blood (3 ml) was withdrawn from each dog through a cannula inserted into the cephalic vein.

Oral Administration Studies: Two 0.5 mg triazolam tablets were given to each dog with 50 ml of water. Blood samples were taken from the cephalic vein at 0 min before administration and 15, 30, 45, 60, 120, 180, 240, 300, 360 and 420 min after administration. The plasma samples were stored frozen until gas chromotographic assay for triazolam.

Nasal Administration Studies: Thirty milligrams of triazolam powder was dissolved in 5 ml of PEG 400 warmed at 55°–60° C. After the solution was cooled to room temperature, an equal volume of 1% methocel J5MS (Dow Chemical Company, Midland, Mich.) solution was mixed with the triazolam solution. Air bubbles generated during mixing were removed by centrifugation. The final concentration of triazolam in the solvent mixture was assayed by an HPLC method. An Altex C18, 4.6×150 mm column was used. The mobile phase contained 60% of 0.05 M $KH_2PO_4$ (pH=6.0, T. J. Baker) and 40% acetonitrile (Fisher Scientific). Flow rate of mobile phase was 1 ml/min. The wavelength used was 221 nm. The assayed concentrations of triazolam solution range from 2.632 to 2.508 mg/ml.

Using a metered dose inhaler, triazolam solution was sprayed into both nostrils of the dogs. The dose administered was determined by weighting the bottle containing the triazolam solution before and after spraying. The dose given to each dog was 0.9343, 1.040, 1.422 and 1.532 mg respectively. Blood sampling times were the same as in the oral study. The plasma samples were frozen until GC assay for triazolam.

GC Assay: To extract triazolam, 0.5 ml of plasma, 50 $\mu$l of internal standard (55 ng/ml clonazepam in methanol) and 3 ml of hexane/methylene chloride (4:3) were vortexed together for 15 seconds and centrifuged for 4 minutes. The bottom aqueous layer was frozen by dry ice/acetone and the upper organic layer was transferred to another tube containing 1 ml of distilled water. The mixture was vortexed for 15 seconds and centrifuged for 4 minutes. Two ml of the upper organic layer was then pipetted into another tube and evaporated to dryness in an vortex-evaporator. Fifty ml of toluene was used for reconstitution.

The amount of triazolam in 3 ml of extract plasma was assayed by an HP model 5830A GC-EC. The glass column used was a 6'×¼" 2 mm on column w/o liner 6" coil (Anspec) with 3% OV-17 chromosorb injector port and detector were 275°, 310° and 350° C., respectively. The flow rate for argon/methane (95:5) gas 42 ml/min.

Results

The average dose-corrected plasma concentration of triazolam for the dogs after oral and nasal administration of triazolam are shown shown in FIG. 1. Plasma triazolam levels after nasal administration were consistently higher than those for oral administration The oral plasma concentration-time curve shows more variability than with nasal administration. This is attributable to variability in gastric emptying of the tablets. Table 1 shows the various relevant pharmacokinetic parameters obtained from this study.

There was significant nasal absorption of triazolam. The mean AUC after nasal administration was 2.4-fold larger than that of oral route. Mean plasma triazolam concentration peaked at about 18.8 min. after nasal administration while that of oral route was about 48.8 min. The mean half-life was about the same in both routes of administration. The mean, peak plasma concentration was 27.6 ng/ml for nasal route and 7.0 ng/ml for oral administration. Thus nasal administration provided triazolam both sooner and in a greater amount than oral administration.

EXAMPLE 2

The efficacy of oral versus nasal administration of midazolam was examined using the methodology of Example 1, but modified to allow at least three weeks between studies.

Oral Administration Studies: Five mg equivalent of midazolam free base solution was given to each of four dogs with 50 ml of water. Blood samples were taken from the cephalic vein at 0 min before administration and 15, 30, 45, 60, 90, 120, 180, 240, 300, 360 min after administration. The plasma samples were stored frozen until GC assay for midazolam.

Nasal Administration Studies: 55.6 milligrams of midazolam HCl powder was dissolved in 4 ml of distilled water. One ml of 7.5% methocel J5MS (Dow Chemical Company, Midland, Mich.) solution was mixed with the midazolam solution. Air bubbles generated during mixing were removed by centrifugation. The pH of the solution was 3.62.

Midazolam solution was sprayed, using a meter dose inhaler into both nostrils of the dogs. The dose given to each dog was 7.85, 7.89, 7.22, 5.61 mg free base. Blood sampling times were the same as in the oral study. The plasma samples were frozen until GC assay for midazolam.

GC Assay—for extraction, 0.5 ml of plasma, 100 μl of internal standard (100 ng/ml flurazepam in methanol) and 0.5 ml of 2N sodium hydroxide were vortexed for 5 seconds. Five ml of hexane was then added and the mixture was vortexed for one min. and centrifuges for 4 minutes. Four ml of the upper organic layer was then pipetted into another tube and evaporated to dryness in an vortex-evaporator. Fifty μl of hexane/isoamyl alcohol (80:20) was used for reconstitution.

Midazolam in plasma was assayed by a Hewlett Packard model 5830A GC-EC. The glass column used was a 6'×¼" 2 mm on column w/o liner 6" coil (Anspec) with 3% OV-17 chromosorb W-HP 80/100 packing (Anspec). The temperatures for column, injector port and detector were 250°, 310° and 310° C., respectively. The flow rate for argon/methane (95:5) gas was 33 ml/min.

Results and Discussion

The average dose-corrected plasma concentrations of midazolam for the dogs after oral and nasal administration of midazolam is shown in FIG. 2. Plasma midazolam levels after nasal administration were consistently higher than after oral administration.

Table 2 shows various relevant pharmacokinetic parameters obtained from this study. The AUCs listed under nasal and oral administration were normalized with the dose administered. There was a mean of 2.5-fold increase in AUC after nasal administration. The Cmax after oral administration was 4 times lower than that of nasal route. The Tmax after nasal administration was 2-fold earlier than after oral administration. The mean half-life was about the same in both routes of administration. There was significant increase in bioavailability of midazolam after nasal versus oral administration.

EXAMPLE 3

The efficacy of oral versus nasal administration was examined using the methodology of Example 2.

Oral Administration Studies: Fifteen mg of flurazepam HCl solution was given to each dog with 50 ml of water. Blood samples were taken from the cephalic vein at 0 min before administration and at 15, 30, 45, 60, 120, 180, 240, 300, 360 min after administration. The plasma samples were stored frozen until GC assay for flurazepam.

Nasal Administration Studies: One hundred and twenty milligrams of flurazepam HCl powder was dissolved in 4 ml of distilled water. One ml of 7.5% methocel J5MS (Dow Chemical Company, Midland, Mich.) solution was mixed with the flurazepam solution. Air bubbles generated during mixing were eliminated by centrifugation. The pH of the solution was 1.82.

Flurazepam solution was sprayed into both nostrils of the dogs. The dose given to the dogs was 14.5, 12.4, 12.1 and 12.5 mg as flurazepam HCl. Blood sampling times were same as in the oral study. The plasma samples were frozen until GC assay for flurazepam.

GC Assay: For extraction, 0.5 ml of plasma, 50 μl of internal standard (100 ng/ml diazepam in methanol) and 0.5 ml of 2N sodium hydroxide were vortexed for 5 seconds. Five ml of hexane was then added and the mixture was vortexed together for one min. and centrifuged for 4 minutes. Four ml of the upper organic layer was then pipetted. Fifty μl of hexane/isoamyl alcohol was used for reconstitution.

Flurazepam in plasma was assayed by a Hewlett Packard model 5830A GC-EC. The glass column used was a 6'×¼" 2 mm on column w/o liner 6" coil (Anspec) with 3% OV-17 chromosorb W-HP 80/100 packing (Anspec). The temperatures for column, injector port and detector were 250°, 310° and 310° C., respectively. The flow rate for argon/methane (95:5) gas was 33 ml/min.

Results and Discussion

The average dose-corrected plasma concentrations of flurazepam for each dog after oral and nasal administration of flurazepam are shown in FIG. 3. Plasma flurazepam levels after nasal administration were consistently higher than after oral administration.

Table 3 shows relevant pharmacokinetic parameters obtained from this study. The AUC for oral administration was estimated up to the last data point because flurazepam was still in its distribution phase As a result, half-life of the compound was not calculated. The AUCs listed under nasal and oral administration were normalized with the dose administered. There was a mean of 51-fold increase in AUC after nasal administration. The Cmax after oral administration was 15 times lower than that of nasal route. The Tmax after nasal administration was half that of oral route.

EXAMPLE 4

A variety of hypnotics including chloral hydrate, sodium pentobarbital and flurazepam were administered to Wistar rats to compare the efficacy of oral and nasal administration. Because the rats proved resistant to flurazepam by oral technique, no comparison of that compound was possible.

Oral Administration Studies: The subjects were fasted for approximately 18 hours; water was available ab libitum. Aqueous solutions of chloral hydrate obtained from Sigma Chemical Co., Ltd. and sodium pentobarbital were separately administered to groups of the subject rats using a constant dose volume of 10mg/kg. Different dosage levels were obtained by varying the aqueous concentrations of therapeutic drug to identify an effective amount of hypnotic.

The animals were then placed in a constant temperature environment of 32° C. The duration of sleeping time (measured by the loss and reappearance of the righting reflex) was recorded for each animal. The results within each group were then averaged.

Nasal Administration Studies: The methodology of the oral studies was repeated with substitution of nasal administration of aqueous solutions through a fine catheter inserted into the nostril. The therapeutic drug was dosed at a constant volume of 50 $\mu$l which would deliver an amount of the hypnotic which would be orally effective.

Results and Discussion

Wide variation of results between similarly treated subjects occurred for nasal administration. That variation was attributed to expulsion, as by sneezing, swallowing or inhalation. All of these physiological responses interfered with administration. Despite this interference, the data confirmed that these hypnotics, in contrast to benzodizaepines, are significantly less effective where administered nasally than by conventional technique.

The foregoing Examples are illustrative of the present invention. The scope of this invention is indicated by the appended claims, and all changes which come within the meaning and range of equivalency of these claims are intended to be embraced therein.

What is claimed is:

1. A composition for the administration of a hypnotic drug comprising a systemically effective amount of a benzodiazepine in a pharmaceutically acceptable nasal carrier.

2. The composition of claim 1, wherein the hypnotic drug comprises the free base or pharmaceutically acceptable salt of a benzodiazepine.

3. The composition of claim 1, wherein the benzodiazepine is totally solubilized in the carrier.

4. The composition of claim 2, wherein a portion of the benzodiazepine is dispersed in undissolved form in the carrier.

5. The composition of claim 2, wherein the benzodiazepine comprises triazolam.

6. The composition of claim 2, wherein the benzodiazepine comprises midazolam.

7. The composition of claim 2, wherein the benzodiazepine comprises temazepam.

8. The composition of claim 2, wherein the benzodiazepine is diazepam.

9. The composition of claim 2, wherein the benzodiazepine comprises flurazepam.

10. A method for inducing an improved pharmacological response in a mammal comprising the nasal administration of a composition comprising a systemically effective amount of a benzodiazepine in a pharmaceutically acceptable nasal carrier.

11. The method of claim 10, wherein the benzodiazepine is essentially totally solubilized in the carrier to induce an improved onset of pharmacological response.

12. The method of claim 10, wherein the composition is nasally administered to a human subject in an amount effective for the improvement of sleep.

13. The composition of claim 2, wherein the pharmaceutically acceptable salt of a benzodiazepine is a carboxylic acid salt having from about 10 to about 30 carbon atoms.

14. The method of claim 10, wherein the pharmaceutically acceptable salt of a benzodiazepine is a carboxylic acid salt having from about 10 to about 30 carbon atoms.

15. The composition of claim 2, wherein the benzodiazepine is in a solution, suspension or gel composed in major amount of water.

16. The method of claim 10, wherein the benzodiazepine is in a solution, suspension or gel composed in major amount of water.

* * * * *